(12) United States Patent
Bowers, II et al.

(10) Patent No.: US 8,833,140 B2
(45) Date of Patent: Sep. 16, 2014

(54) OPTICALLY HEATED ANALYTE DESORBER FOR GAS CHROMATOGRAPHY ANALYSIS

(75) Inventors: Michael J. Bowers, II, Sykesville, MD (US); Tadd C. Kippeny, Mount Airy, MD (US)

(73) Assignee: BAE Systems Information and Electronic Systems Integration Inc., Nashua, NH (US)

( * ) Notice: Subject to any disclaimer, the term of this patent is extended or adjusted under 35 U.S.C. 154(b) by 324 days.

(21) Appl. No.: 13/467,074

(22) Filed: May 9, 2012

(65) Prior Publication Data

US 2014/0026638 A1    Jan. 30, 2014

Related U.S. Application Data

(60) Provisional application No. 61/508,809, filed on Jul. 18, 2011.

(51) Int. Cl.
| | | |
|---|---|---|
| *G01N 1/44* | (2006.01) | |
| *G01N 1/28* | (2006.01) | |
| *B01J 20/281* | (2006.01) | |

(52) U.S. Cl.
CPC .................................. *G01N 30/482* (2013.01)
USPC ....................... 73/23.41; 73/31.07; 73/863.12

(58) Field of Classification Search
CPC ....... G01N 30/482; G01N 30/93; G01N 1/02; G01N 1/22; G01N 1/44; G01N 1/405; G01N 2030/0095
USPC ............ 73/23.41, 23.42, 19.01, 19.12, 31.07, 73/863.11, 863.21, 863.83
See application file for complete search history.

(56) References Cited

U.S. PATENT DOCUMENTS

| | | | | |
|---|---|---|---|---|
| 4,518,699 | A * | 5/1985 | Bohl | 73/863.53 |
| 4,698,314 | A * | 10/1987 | Tao | 436/171 |
| 6,171,378 | B1 * | 1/2001 | Manginell et al. | 96/143 |
| 6,802,227 | B2 * | 10/2004 | Lindgren et al. | 73/863.12 |
| 6,895,804 | B2 * | 5/2005 | Lovell et al. | 73/31.05 |
| 7,047,661 | B2 * | 5/2006 | Alcaraz et al. | 34/218 |
| 7,299,679 | B2 * | 11/2007 | Lovell et al. | 73/31.05 |
| 7,416,902 | B2 * | 8/2008 | Pletcher et al. | 73/31.07 |

(Continued)

OTHER PUBLICATIONS

Pawliszyn, Janusz, and Shi Liu. "Sample introduction for capillary gas chromatography with laser desorption and optical fibers." Analytical Chemistry 59.10 (1987): 1475-1478.*

*Primary Examiner* — Lisa Caputo
*Assistant Examiner* — Punam Roy
(74) *Attorney, Agent, or Firm* — Maine Cernota & Rardin; Douglas P. Burum; Daniel J. Long

(57) ABSTRACT

Analytes are rapidly desorbed from a carbonaceous sorbent powder with improved quantitation and reduced analyte re-adsorption, thermal degradation, and rearrangement. The sample is distributed in a thin layer onto a desorption surface within a chamber. The layer can be a monolayer. Heating light irradiates the sample through a window, directly and rapidly heating the sample while the desorbed analytes diffuse into a vacuum or are removed by a carrier gas. Finally, the sorbent is flushed from the chamber by a transport gas. The desorption surface can be an inner surface of the window, or a surface of a porous frit that divides the chamber into two sections. The frit can be stainless steel or glass. The carrier gas can be helium, argon, or carbon dioxide. The light source can be a tungsten halogen lamp. A heater can control the chamber temperature according to a heating profile.

27 Claims, 8 Drawing Sheets

(56) References Cited

U.S. PATENT DOCUMENTS

| | | |
|---|---|---|
| 7,511,809 B2 * | 3/2009 | Schneider et al. ............ 73/31.07 |
| 7,687,276 B2 * | 3/2010 | Kunz ............................ 436/164 |
| 7,815,722 B2 * | 10/2010 | Yeatman et al. ................ 96/143 |
| 7,833,802 B2 * | 11/2010 | Henry et al. ................... 436/155 |
| 8,365,575 B2 * | 2/2013 | Kippeny ....................... 73/23.41 |
| 2002/0182746 A1 * | 12/2002 | Mester et al. .................. 436/178 |
| 2007/0248500 A1 * | 10/2007 | Pawliszyn et al. ............ 422/101 |
| 2012/0264227 A1 * | 10/2012 | Couch ........................... 436/173 |

\* cited by examiner

OPTICALLY HEATED ANALYTE DESORBER FOR GAS CHROMATOGRAPHY ANALYSIS

RELATED APPLICATIONS

This application claims the benefit of U.S. Provisional Applications No. 61/508,809, filed Jul. 18, 2011 which is herein incorporated by reference in its entirety for all purposes.

STATEMENT OF GOVERNMENT INTEREST

The invention was made with United States Government assistance under contract no. HR0011-08-C-0056 awarded by the Defense Advanced Research Projects Agency (DARPA). The United States Government has certain rights in the invention.

FIELD OF THE INVENTION

The invention relates to apparatus and methods for desorption of analytes from sorbent materials for gas chromatography analysis, and more particularly, to heat-induced desorption of analytes adsorbed on carbonaceous sorbent materials.

BACKGROUND OF THE INVENTION

A common method of collecting a sample for analysis by gas chromatography is "solid phase micro-extraction," or SPME. In this method, a sorbent material is exposed to an environment containing analytes, causing some of the analytes to be adsorbed onto the sorbent material. The sorbent material is then transferred to a container, connected to the injection port of the gas chromatograph, and heated so as to cause the adsorbed analytes to be desorbed and carried by an inert carrier gas into the gas chromatograph. Typically, the sorbent material is indirectly heated by conventional thermal transfer, whereby the container is directly heated, and the heat is allowed to flow into the sorbent material indirectly by thermal conduction.

This indirect heating desorption process can be slow and inefficient, and attempts to speed up the process by applying more heat may lead to thermal degradation and rearrangement of the analytes. Also, desorption utilizing indirect thermal conduction heating can decrease the uniformity of the analyte retrieval, thereby leading to inaccurate quantitative analysis, especially when applied to a carbonaceous sorbent material that has poor heat conductivity, and particularly for large, high boiling point analytes. Frequently, the sorbent material is configured in a long, narrow bed to avoid breakthrough of the analytes. This geometry greatly compounds the difficulty of obtaining quantitative results.

What is needed, therefore, is an apparatus and method for rapid desorption of analytes from carbonaceous sorbent materials with reduced re-adsorption and correspondingly improved quantitative results, and with reduced thermal degradation and rearrangement of the adsorbed analytes.

SUMMARY OF THE INVENTION

A novel apparatus and method provide rapid desorption of analytes from a carbonaceous sorbent powder sample with reduced re-adsorption and correspondingly improved quantitative results, and with reduced thermal degradation and rearrangement of the adsorbed analytes. According to the invention, the entire sorbent powder sample is simultaneously and uniformly heated in a rapid, efficient, manner by distributing the sample onto a desorbing surface within an enclosed chamber in a uniformly thin layer, and directly irradiating the sample with a heating light source. In embodiments, the thin layer is approximately one powder granule in thickness, so that substantially all of the powder granules are heated simultaneously.

Because the carbonaceous sorbent is a strong black body light absorber, direct adsorption of light energy from illumination of the sorbent powder causes a very rapid and intense heating of the particle skin to a depth of several microns, thus eliminating the reliance on indirect thermal transfer. This intense surface heating causes a quick and efficient thermal desorption, without overheating and therefore with reduced thermal degradation and reduced rearrangement of the analyte molecules before their release from the carbonaceous surface.

While the sorbent is heated by the light irradiation, the desorbed analytes are transported away from the sorbent and into the gas chromatograph. In some embodiments, a partial vacuum is created within the desorption chamber, and the analytes diffuse away from the sorbent and into the gas chromatograph. In other embodiments, the desorbed analytes are carried away by a carrier gas. After the desorption process is completed, the sorbent sample is flushed from the chamber by a transport gas so that a new sample can be introduced.

In one general aspect of the present invention, the sorbent is distributed onto a porous frit that divides the chamber into upper and lower sections. The sample is then irradiated with heating light that shines from above through a window in the chamber and onto the frit. In some embodiments, a partial vacuum is created in the desorption chamber and the desorbed analytes diffuse away from the sample, through the frit, and into the gas chromatograph. In other embodiments the desorbed analytes are carried away from the sorbent by an inert carrier gas that flows through the upper section, through the sample and the frit, into the lower section, and into the gas chromatograph, thereby transporting the desorbed analytes into the gas chromatograph. In some of these embodiments, the sample is carried by the transport gas into the upper section through a central pipe, so that it is sprayed against the window and then settles onto the porous frit. And in certain of these embodiments, after desorption of the analytes, the sorbent is flushed from the upper section by the transport gas through the same central pipe.

In another general aspect of the present invention, the sorbent sample is distributed directly onto a window in a lower section of the enclosed chamber. The sample is irradiated with heating light through the window from below. In some embodiments, a partial vacuum is created in the desorption chamber and the desorbed analytes diffuse away from the sample and into the gas chromatograph. In other embodiments, an inert carrier gas transports the desorbed analytes away from the sorbent and into the gas chromatograph. In embodiments, a porous frit divides the lower section from an upper section of the enclosed chamber, and the desorbed analytes pass through the porous frit and the upper section before entering the gas chromatograph, thereby preventing any of the sorbent from being carried into the gas chromatograph together with the analytes. In some of these embodiments, the sample is carried by the transport gas into the lower section through a central pipe and sprayed onto the window. And in certain of these embodiments, the sorbent is flushed from the lower section by the transport gas through the same central pipe.

In embodiments of both general aspects, the porous frit is either stainless steel or glass. In various embodiments, the sorbent material is divided into a plurality of samples, and only one sample at a time is introduced into the apparatus for desorption. In some of these embodiments, the desorption and analysis is repeated using successive samples. And in various embodiments, at least one of the samples is deposited into a collection vial for future analysis and/or comparison.

Due to the wide spectrum of absorption that is characteristic of black body carbonaceous sorbents, embodiments can use almost any source of heating light ranging in wavelength from UV to IR. In some embodiments, the heating light originates from a tungsten halogen lamp.

In embodiments, at least one of the carrier gas and the transport gas is helium, argon, carbon dioxide, or nitrogen. And in various embodiments the gas chromatograph is cooperative with a cryogenic trap that includes at least two valves configured to bypass the cryogenic trap.

One general aspect of the present invention is a system for rapidly desorbing analytes from a carbonaceous sorbent powder for introduction into a gas chromatograph. The system includes a sealed desorption chamber, a desorption surface within the desorption chamber onto which the sorbent powder can be deposited, the sorbent powder having analytes adsorbed thereupon, a transport gas system configured to transport the sorbent powder with a transport gas into the desorption chamber and to deposit the sorbent powder onto the desorption surface as a substantially uniform layer of sorbent powder granules, the transport gas system being further configured to remove the sorbent powder from the desorption chamber after desorption of the analytes therefrom, a heating light source located outside of the desorption chamber, a window included in a wall of the deposition chamber and positioned so as to allow light from the heating light source to uniformly illuminate all of the uniform monolayer of sorbent powder, absorption of the heating light by the sorbent powder causing desorption of the analytes therefrom, and an analyte removal system configured to transport desorbed analytes away from the sorbent powder out of the desorption chamber, and into the gas chromatograph.

In some embodiments, the analyte removal system is a vacuum removal system configured to impose a partial vacuum in the desorption chamber and to allow the desorbed analytes to diffuse away from the sorbent and into the gas chromatograph. In other embodiments the analyte removal system is a carrier gas system configured to cause a carrier gas to flow into proximity with the sorbent powder and to carry the desorbed analytes away from the sorbent powder. In some of these embodiments the carrier gas is one of helium, argon, or carbon dioxide. In other of these embodiments the carrier gas system provides a carrier gas flow rate of 300 cc per minute with helium as the carrier gas. And still other of these embodiments further include a carrier gas flow adaptor configured to deliver the carrier gas and analytes to a cryogenic trap of the gas chromatograph and to vent the carrier gas after delivery of the analytes to the cryogenic trap, the adaptor being further configured to short-circuit a cryogenic trap pressure regulation system back onto itself and to isolate the pressure regulation system from the cryogenic trap while the analytes are being carried by the carrier gas into the cryogenic trap.

In various embodiments the transport system is configured to deposit the sorbent powder onto the desorption surface as a substantially uniform monolayer of sorbent powder granules. In some embodiments, the desorption surface is an inner surface of the window.

In certain embodiments the desorption chamber includes a porous frit that divides the desorption chamber into a lower section and an upper section. In some of these embodiments the porous frit is made of either glass or steel. In other of these embodiments a surface of the porous frit is the desorption surface.

In various embodiments the desorption system includes a central pipe through which the transport gas carries the sorbent into the desorption chamber. In some of these embodiments the analyte removal system is a carrier gas system configured to cause a carrier gas to flow into proximity with the monolayer of sorbent powder and to carry the desorbed analytes away from the sorbent powder, and the carrier gas system introduces the carrier gas into the desorption chamber through the central pipe. In other of these embodiments the transport gas removes the sorbent powder from the desorption chamber through the central pipe.

In certain embodiments the transport gas is one of helium, argon, carbon dioxide, and nitrogen. In some embodiments the heating light source is a tungsten halogen lamp.

Various embodiments further include a heating system configured to heat the desorption chamber to a temperature above ambient. In some of these embodiments the heating system is configured to control a temperature of the desorption chamber according to a heating profile.

And in certain embodiments the transport gas system is configured to divide the sorbent powder into a plurality of samples, and to deliver one of the samples to the desorption surface while withholding at least one of the samples from the desorption chamber.

Another general aspect of the present invention is a method for desorbing analytes from a carbonaceous sorbent powder and introducing the analytes into a gas chromatograph. The method includes causing a transport gas to deliver the carbonaceous sorbent powder with analytes adsorbed thereon onto a desorption surface within a desorption chamber, the sorbent powder being distributed onto the desorption surface as a substantially uniform layer of powder granules, uniformly illuminating substantially all of the sorbent granules simultaneously with a heating light delivered through a window in a wall of the desorption chamber from a light source located outside of the desorption chamber, absorption of the heating light by the powder granules causing desorption of the analytes therefrom, during the illumination of the sorbent powder, transporting the analytes away from the sorbent powder, out of the desorption chamber and into a gas chromatograph, and after desorption of the analytes and transporting of the analytes, causing the transport gas to remove the sorbent powder from the desorption chamber.

In embodiments transporting the analytes away from the sorbent powder, out of the desorption chamber and into a gas chromatograph includes creating a partial vacuum within the desorption chamber and allowing the desorbed analytes to diffuse away from the sorbent and into the gas chromatograph.

In certain embodiments transporting the analytes away from the sorbent powder, out of the desorption chamber and into a gas chromatograph includes causing a carrier gas to flow in proximity to the sorbent powder and thereby causing the carrier gas to carry the desorbed analytes away from the sorbent powder and into the gas chromatograph. Some of these embodiments further include isolating a GC pressure controller from a cryogenic trap while the carrier gas delivers the analytes to the cryogenic trap, and directly venting the carrier gas after it has delivered the analytes to the cryogenic trap.

In various embodiments the sorbent powder is distributed onto the desorption surface as a substantially uniform monolayer of powder granules.

In some embodiments the desorption surface is an inner surface of the window.

In certain embodiments the desorption chamber includes a porous frit that divides the desorption chamber into upper and lower sections and prevents sorbent powder from traveling together with the analytes through the frit and into the gas chromatograph. And in some of these embodiments the desorption surface is a surface of the porous frit.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and not to limit the scope of the inventive subject matter.

DETAILED DESCRIPTION

The present invention is a novel apparatus and method for providing rapid desorption of analytes from a carbonaceous sorbent powder sample with reduced re-adsorption and correspondingly improved quantitative results, and with reduced thermal degradation and rearrangement of the adsorbed analytes. According to the invention, the entire sorbent powder sample is simultaneously and uniformly heated in a rapid, efficient, manner by distributing the sample onto a desorbing surface within an enclosed chamber in a uniformly thin layer, and directly irradiating the sample with a heating light source. In embodiments, the thin layer is approximately one powder granule in thickness, so that substantially all of the powder granules are heated simultaneously.

Because the carbonaceous sorbent is a strong black body light absorber, direct adsorption of light energy from illumination of the sorbent powder causes a very rapid and intense heating of the particle skin to a depth of several microns, thus eliminating the reliance on indirect thermal transfer. This intense surface heating causes a quick and efficient thermal desorption, without overheating and therefore with reduced thermal degradation and reduced rearrangement of the analyte molecules before their release from the carbonaceous surface.

While the sorbent is heated by the light irradiation, the desorbed analytes are transported away from the sorbent and into the gas chromatograph. In some embodiments, a partial vacuum is created within the desorption chamber, and the analytes diffuse away from the sorbent and into the gas chromatograph. In other embodiments, the desorbed analytes are carried away by a carrier gas. After the desorption process is completed, the sorbent sample is flushed from the chamber by a transport gas so that a new sample can be introduced.

Figure 1A:
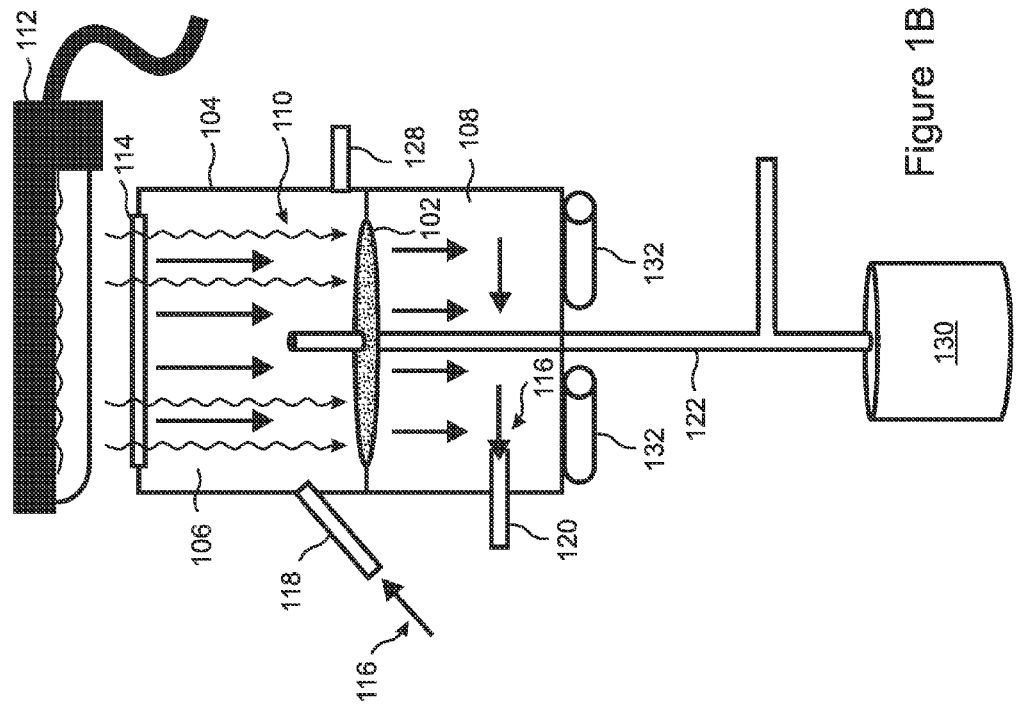
FIG. 1A is a functional diagram illustrating transport of a sorbent sample by a transport gas through a central pipe and into a desorption chamber in an embodiment of the present invention for which the desorption surface is the upper surface of a porous frit.

With reference to FIG. 1A, in one general aspect of the present invention the enclosed chamber 104 is divided into an upper section 106 and a lower section 108 by a porous frit 102. In embodiments, the chamber 104 is of a modular design utilizing gas tight seals. The sorbent 100 is carried into the upper section 106 by a transport gas 126 and distributed onto the porous frit 102, while the transport gas 126 exits the chamber through a transport gas port 128.

Figure 1B:
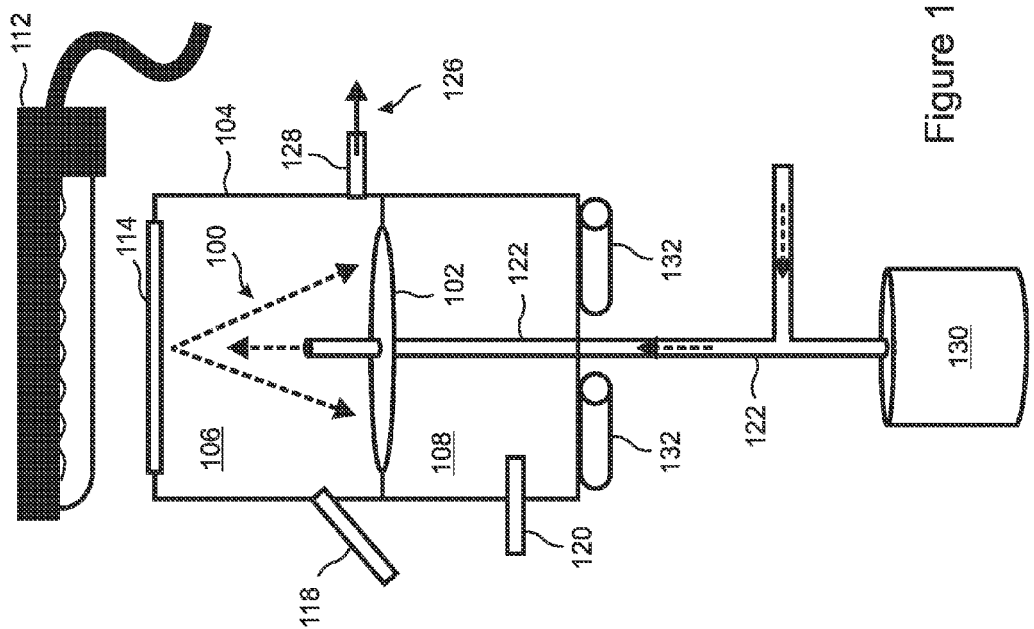
FIG. 1B is a functional diagram illustrating illumination by a heating light of the sample deposited in FIG. 1A while a carrier gas enters the chamber through a carrier gas port and flows through the sample.

With reference to FIG. 1B, the sample 100 is then irradiated with heating light 110 from a lamp 112 or other light source that shines light onto the sample 100 from above through a window 114 in the chamber 104. In the embodiment of FIG. 1B, an inert carrier gas 116 flows into the upper section 106 through a carrier gas inlet port 118, through the sample 100 and the frit 102, into the lower section 108, and out through a carrier gas exit port 120 into the gas chromatograph (not shown), thereby carrying the desorbed analytes into the gas chromatograph. In similar embodiments, a partial vacuum is created within the desorption chamber 104, and the desorbed analytes diffuse away from the sample 100, through the frit 102, through the lower section 108, and into the gas chromatograph.

In embodiments, the distribution of the sorbent sample 100 on the frit 102 is sufficiently uniform and thin so as to ensure that substantially all of the sample granules are directly irradiated by the heating light 110. In various embodiments, the apparatus further includes one or more heating units 132 that are configured to control the temperature of the enclosed chamber 104. This ensures that the desorbed analytes do not condense on the chamber walls or other elements of the desorption system. In some embodiments the chamber temperature is held constant, while in other embodiments the chamber temperature is varied according to a desired temperature profile, such as a ramped temperature profile.

Figure 1C:
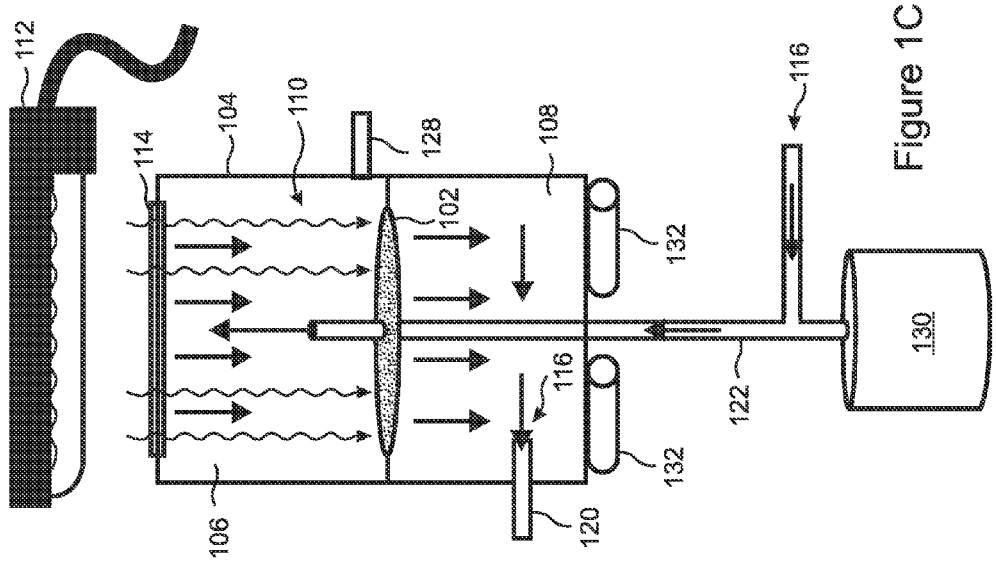
FIG. 1C is a functional diagram similar to FIG. 1B, except that the carrier gas enters the chamber through the central pipe.
Figure 1D:
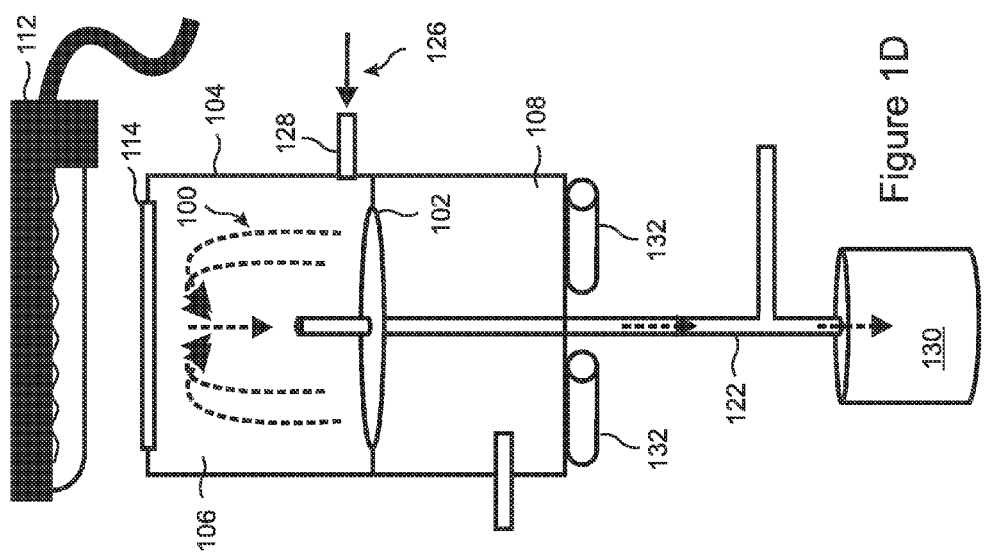
FIG. 1D is a functional diagram illustrating removal of the sorbent from the chamber by a transport gas flowing out through the central pipe.

With reference to FIG. 1A, in some of these embodiments, the sample 100 is carried by the transport gas 126 into the upper section 106 through a central pipe 122. The sample is then sprayed against the window 114, and settles onto the porous frit 102. With reference to FIG. 1C, in various embodiments the carrier gas 116 also enters the upper section 106 through the central pipe 122, so that the flow of carrier gas 116 is directed against the inside of the window 114 so as to break up the carrier gas jet 116 and avoid disturbing the even distribution of the sorbent sample 100. And with reference to FIG. 1D, in some of these embodiments, after desorption of the analytes from the sample 100, the transport gas 126 enters the upper section 106 through the transport gas port 128 and flushes the desorbed sample 100 from the upper section 106 and back out through the central pipe 122.

In embodiments, the porous frit 102 is either stainless steel or glass. In various embodiments, the sorbent material 100 is divided into a plurality of portions, and only one portion at a time is introduced into the apparatus for desorption. In some of these embodiments, the desorption and analysis is repeated using successive portions. And in various embodiments, at least one of the portions is deposited into a collection vial 130 for future analysis and/or comparison.

In embodiments, at least one of the carrier gas 116 and the transport gas 126 is helium, argon, carbon dioxide, or nitrogen. In some embodiments, the heating light 110 originates from a tungsten halogen lamp 112.

Figure 2A:
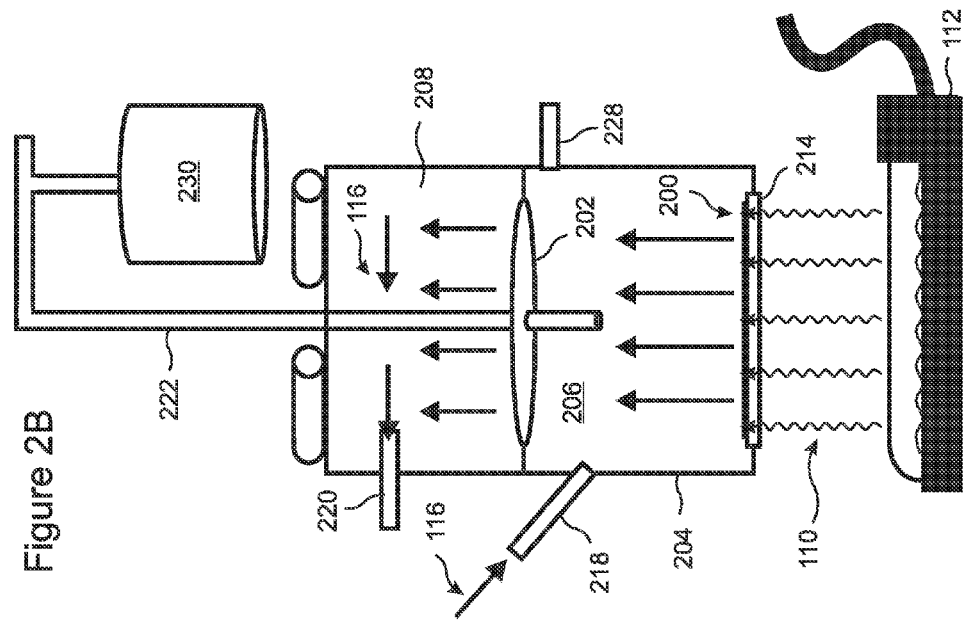
FIG. 2A is a functional diagram illustrating transport of a sorbent sample by a transport gas through a central pipe and into a desorption chamber in an embodiment of the present invention for which the desorption surface is the upper surface of the window.

With reference to FIG. 2A, in another general aspect of the present invention the enclosed chamber 204 is divided into a lower section 206 and an upper section 208 by a porous frit 202. In embodiments, the chamber 104 is of a modular design utilizing gas tight seals. The sorbent 100 is carried into the lower section 206 by a transport gas 126 and distributed onto the porous frit 202, and the transport gas 126 exits the chamber through a transport gas port 228.

Figure 2B:
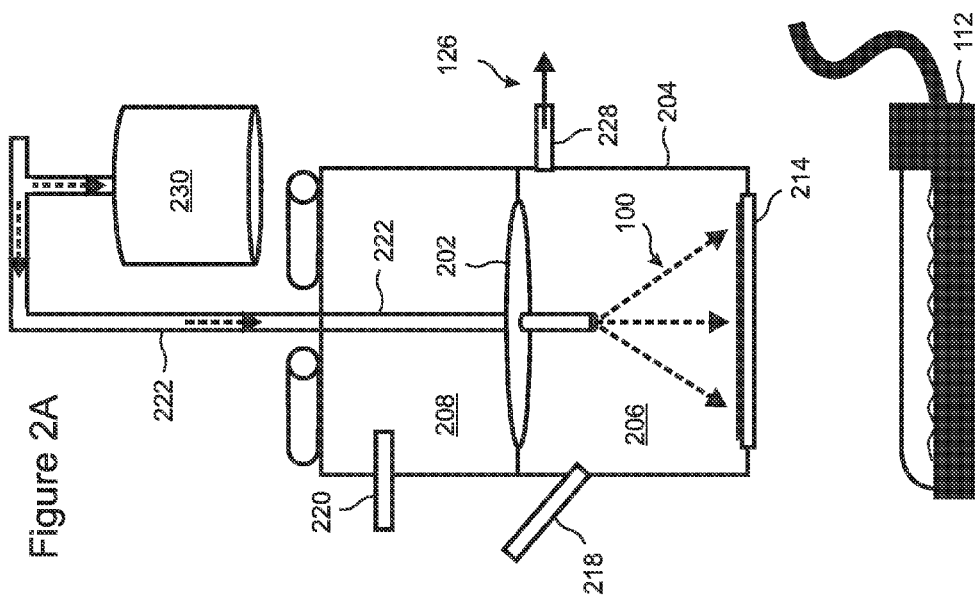
FIG. 2B is a functional diagram illustrating illumination by a heating light of the sample deposited in FIG. 2A while a carrier gas enters the chamber through a carrier gas port and flows through the sample.

With reference to FIG. 2B, the sample 100 is then irradiated with heating light 110 from a lamp 112 or other light source that shines onto the sample 100 from below through a window 214 in the chamber 204. In the embodiment of FIG. 2A, an inert carrier gas 116 flows into the lower section 206 through a carrier gas inlet port 218, past the sample 100, through the frit 202, into the upper section 208, and out through a carrier gas exit port 220 into the gas chromatograph (not shown), thereby carrying the desorbed analytes into the gas chromatograph. In similar embodiments, a partial vacuum is created within the desorption chamber 204, and the desorbed analytes diffuse away from the sample 100, through the frit 202, through the lower section 208, and into the gas chromatograph.

Figure 2D:
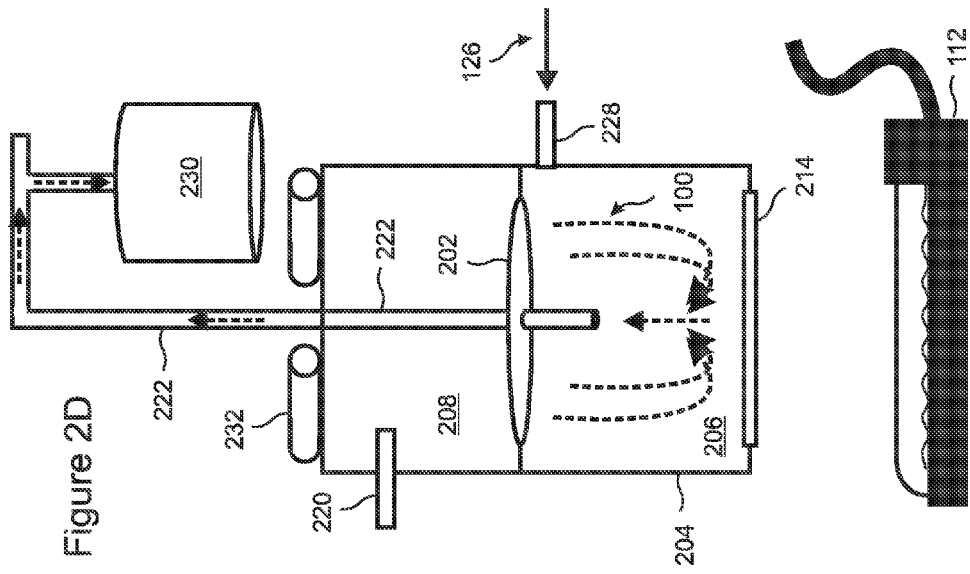
FIG. 2D is a functional diagram illustrating removal of the sorbent from the chamber by a transport gas flowing out through the central pipe.
Figure 2C:
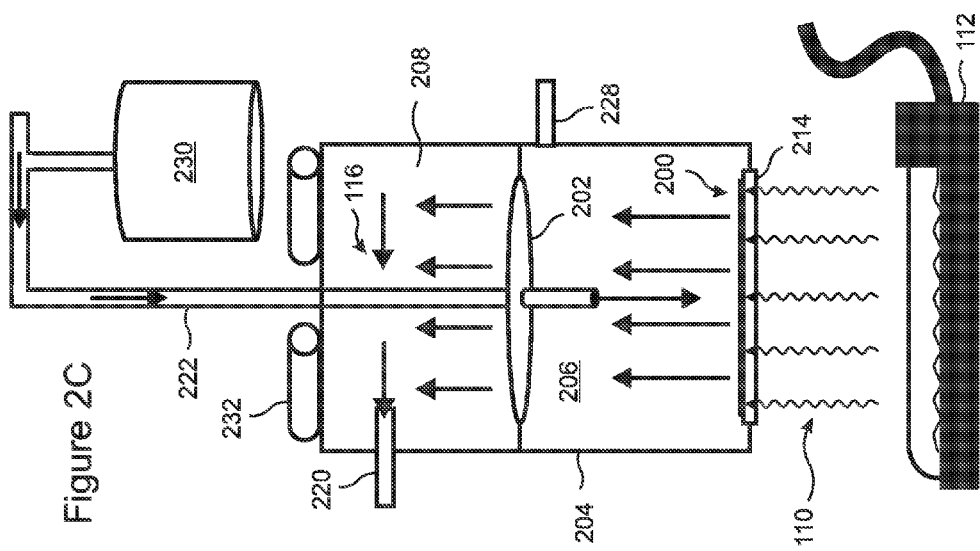
FIG. 2C is a functional diagram similar to FIG. 2B, except that the carrier gas enters the chamber through the central pipe.

With reference to FIG. 2A, in some of these embodiments, the sample 100 is carried by the transport gas 126 into the lower section 206 through a central pipe 222, from which it is sprayed onto the window 214 in a thin, substantially uniform layer. With reference to FIG. 2C, in various embodiments the carrier gas 116 also enters the lower section 206 through the central pipe 222. And with reference to FIG. 2D, in some of these embodiments, after desorption of the analytes from the sample 100, the transport gas 126 enters the lower section 206 through the transport gas port 228 and flushes the desorbed sample 100 from the lower section 206 and back out of the chamber through the central pipe 222.

In embodiments, the distribution of the sorbent sample 100 on the window 214 is sufficiently uniform and thin so as to ensure that substantially all of the sample granules are directly irradiated by the heating light 110. In various embodiments, the apparatus further includes one or more heating units 232 that are configured to control the temperature of the enclosed chamber 204. This ensures that the desorbed analytes do not condense on the chamber walls or other elements of the desorption system. In some embodiments the chamber temperature is held constant, while in other embodiments the chamber temperature is varied according to a desired temperature profile, such as a ramped temperature profile.

In embodiments, the porous frit 202 is either stainless steel or glass. In various embodiments, the sorbent material 100 is divided into a plurality of portions, and only one portion at a time is introduced into the apparatus for desorption. In some of these embodiments, the desorption and analysis is repeated using successive portions. And in various embodiments, at least one of the portions is deposited into a collection vial 230 for future analysis and/or comparison.

In embodiments, at least one of the carrier gas 116 and the transport gas 126 is helium, argon, carbon dioxide, or nitrogen. In some embodiments, the heating light 110 originates from a tungsten halogen lamp 112.

Figure 3:
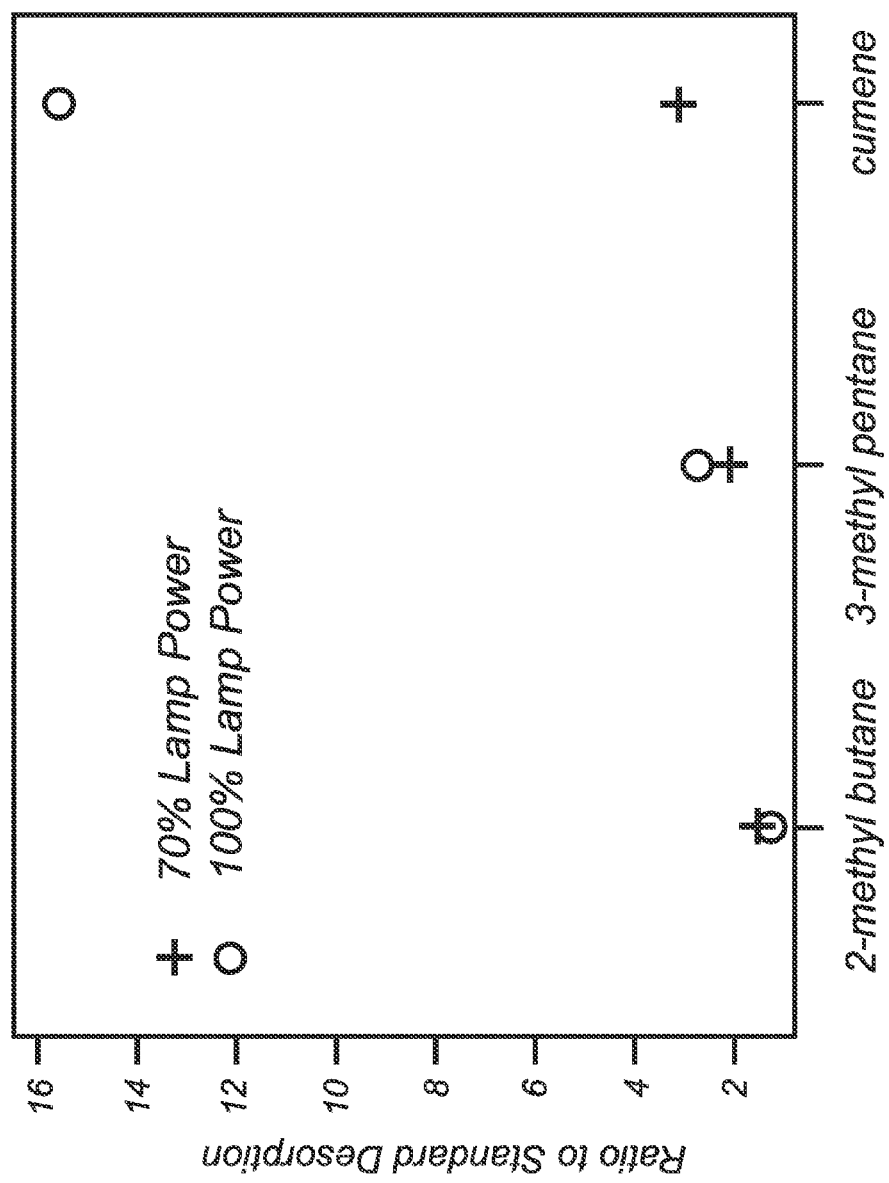
FIG. 3 is a chart that presents desorption data from an embodiment of the present invention for several different analytes and for two different light intensities.

With reference to FIG. 3, comparative measured results are shown illustrating the increase in analyte recovery of the present invention as compared to the prior art. The data are plotted as ratios in which the numerator is an amount of analyte recovered using a standard fast flow desorption tube of the prior art, and the denominator is an amount of analyte recovered using the embodiment of the present invention illustrated in FIGS. 1C and 1D. The analyte recovery for all three of the illustrated compounds is greater for the present invention as compared to the prior art by a factor of between 2 and 3.5 at 70% lamp power. This demonstrates that the thin bed arrangement of the present invention reduces re-adsorption relative to the typical long bed method of the prior art.

It can be seen from FIG. 3 that with increasing illumination power in the thin bed arrangement of the present invention a significant improvement in analyte recovery is observed for larger molecular weight compounds. This is due to increased particle skin temperatures caused by the direct light absorption and heating of substantially every particle in the sorbent sample. In particular, as shown in FIG. 3, cumene (a nine carbon hydrocarbon) shows a 1500% increase in analyte recovery in response to a 30% increase in heating light illumination power. This indicates that the shorter sorbent bed length of the present invention as compared to typical prior art methods improves the efficient escape of the analytes from the sorbent with less re-absorption.

The carrier gas flow rates used in embodiments of the present invention are typically higher than the flow rates anticipated by many gas chromatographs. For example, embodiments of the present invention provide a carrier gas flow rate of 300 cc per minute with helium as a carrier gas, while the flow rates used by a typical cryogenic focusing trap in a gas chromatograph are generally less than 70 cc per minute. Operating the present invention at a slow carrier gas flow would surrender some of the efficiency of the invention, and could lead to results that were less quantitative, since the analytes would have more time to possibly re-adsorb on the sorbent before they were carried away by the carrier gas.

So as to enable standard gas chromatographs and cryogen sampling traps to function with the present invention, embodiments of the present invention include carrier gas flow adaptors that enable the present invention to operate at a desired carrier gas flow rate that is higher than what could normally be tolerated by an unmodified gas chromatograph.

Figure 4A:
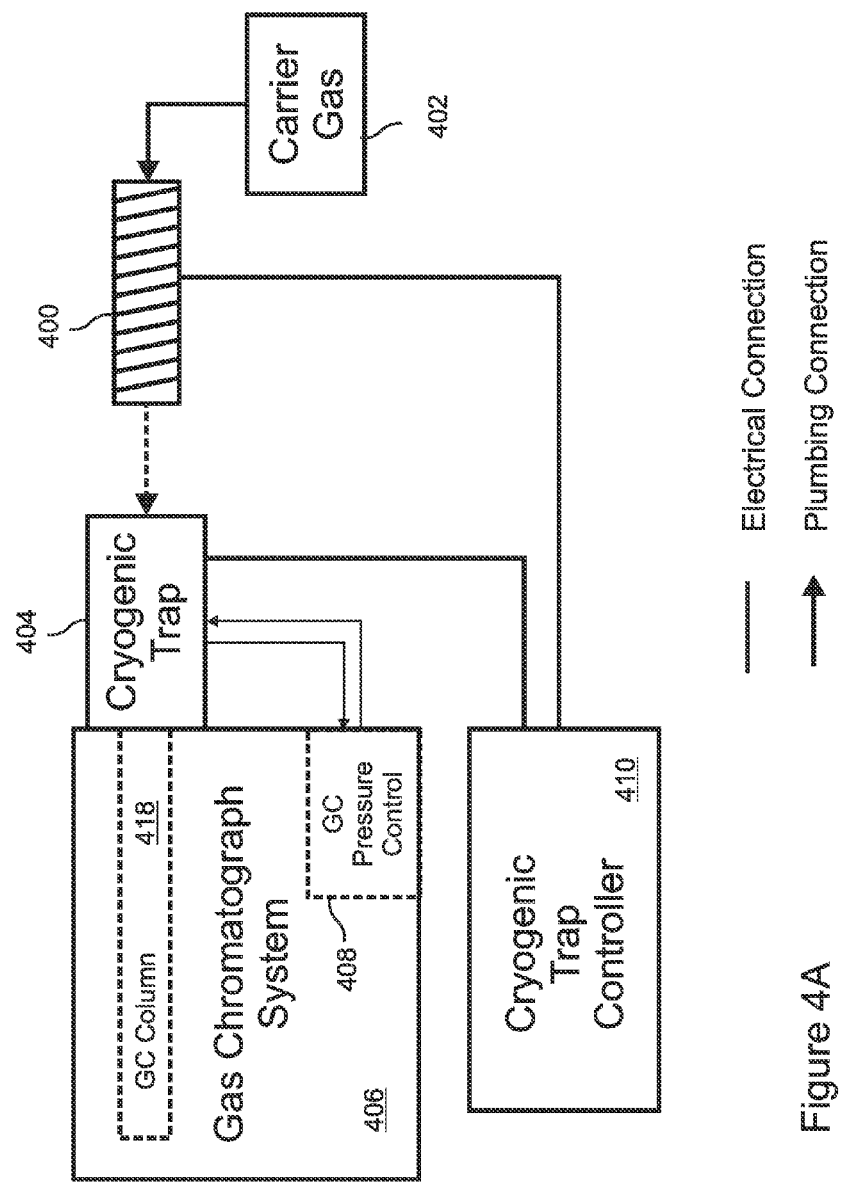
FIG. 4A is a block diagram of a gas chromatograph with a cryogenic trap accepting analytes from an SPME sample in a typical procedure of the prior art.

FIG. 4A is a block diagram that illustrates in a general way how the sampling system functions in a typical gas chromatograph of the prior art. The analytes are initially adsorbed in a sorbent contained in an SPME sample chamber 400. The SPME sample chamber 400 is heated, thereby conductively heating the sorbent and desorbing the analytes. The analytes are carried by a carrier gas 402 into a cryogenic trap chamber 404 where the analytes adhere to the cryogenically cooled walls of the chamber. The cryogenic trap chamber 404 serves as the inlet for the chromatographic column 418 of the gas chromatograph 406.

After collection of the analytes, the flow of carrier gas is stopped, and the cryogenic trap chamber 404 is heated, thereby allowing the analytes to flow into the analyzing column of the gas chromatograph 406. The cycle of heating and cooling of the cryogenic trap chamber 404 and the coordination with the SPME sample chamber 400 is controlled by a cryogenic trap controller 410.

A substantially constant pressure of inert gas is maintained at all times in the cryogenic trap chamber 404 by a GC pressure controller 408 included in the gas chromatograph 406. Excess pressure in the cryogenic trap chamber 404 due to sample injection is vented by a "split vent" in the GC pressure controller 408. Due to the relatively slow heating and desorption in the SPME sample chamber 400, the flow of carrier gas 402 in this prior art example is modest, and can be accepted and vented by the GC pressure controller. However, in embodiments of the present invention, if the SPME sample chamber 400 were simply replaced by the present invention, the much higher carrier gas flow rate would be above the limit that the GC pressure controller 408 can manage, and the system would fail.

Figure 4B:
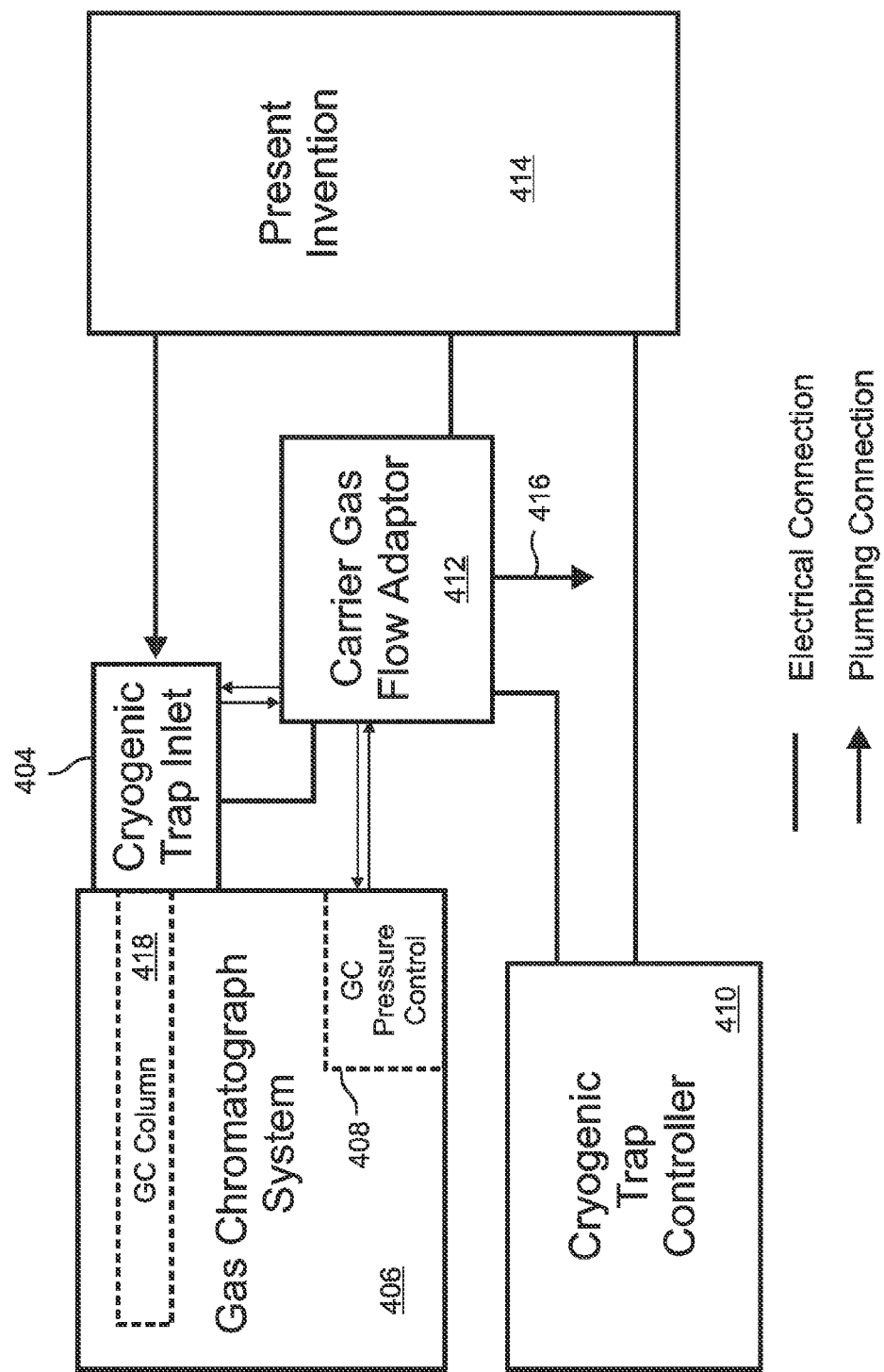
FIG. 4B is a block diagram showing the gas chromatograph and cryogenic trap of FIG. 4A accepting carrier gas and analytes from an embodiment of the present invention that includes a carrier gas flow adaptor.

Referring to FIG. 4B, embodiments of the present invention include a carrier gas flow adaptor 412 that interrupts the flow between the GC pressure controller 408 and the cryogenic trap chamber 404, so that after the analytes are deposited in the cryogenic trap chamber 404 the carrier gas from the desorption chamber of the invention 414 flows out through a vent 416 in the flow adaptor 412, while the regulating flow from the GC pressure controller 408 is temporarily short-circuited back on itself and thereby isolated from the cryogenic trap chamber 404. After all of the analytes have been collected in the cryogenic trap chamber 404 the flow of carrier gas is stopped, and the control paths between the GC pressure controller 408 and the cryogenic trap chamber 404 are restored resume normal operation.

The carrier gas flow adaptor 412 also interrupts the control signals between the cryogenic trap controller 410 and the cryogenic trap chamber 404, so that the switching of the gas flow channels between the GC pressure controller 408 and the cryogenic trap chamber 404 can be coordinate with the stopping and starting of the flow of carrier gas from the desorption chamber 414 and the cooling and heating of the cryogenic trap chamber 404.

Figure 5B:
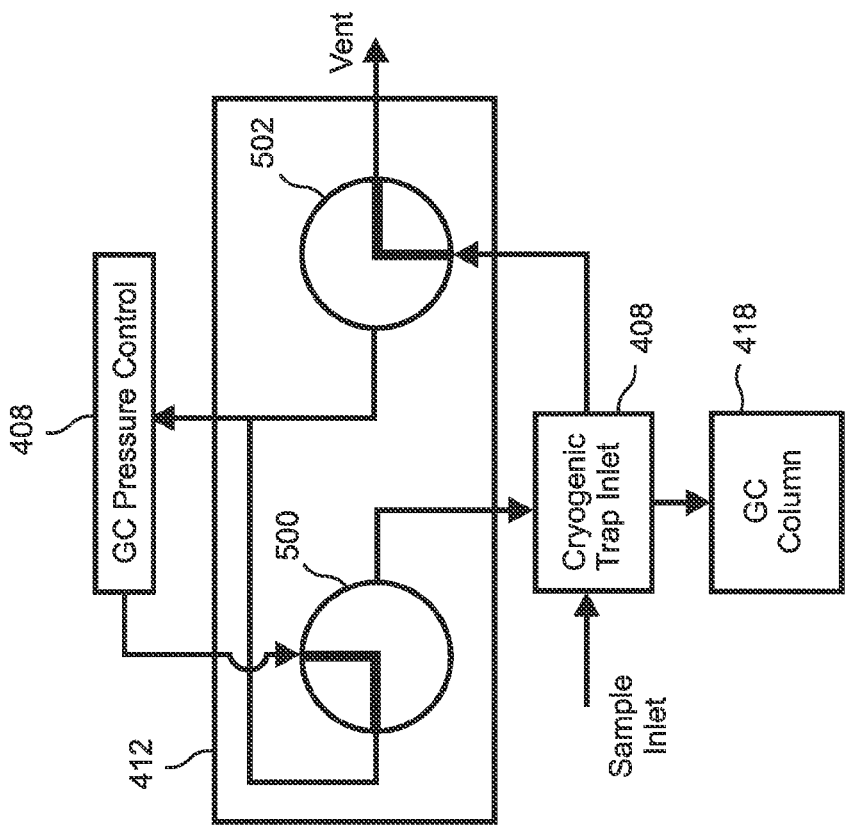
FIG. 5B is a block diagram of the carrier gas flow adaptor of FIG. 5A shown in the by-passed configuration.
Figure 5A:
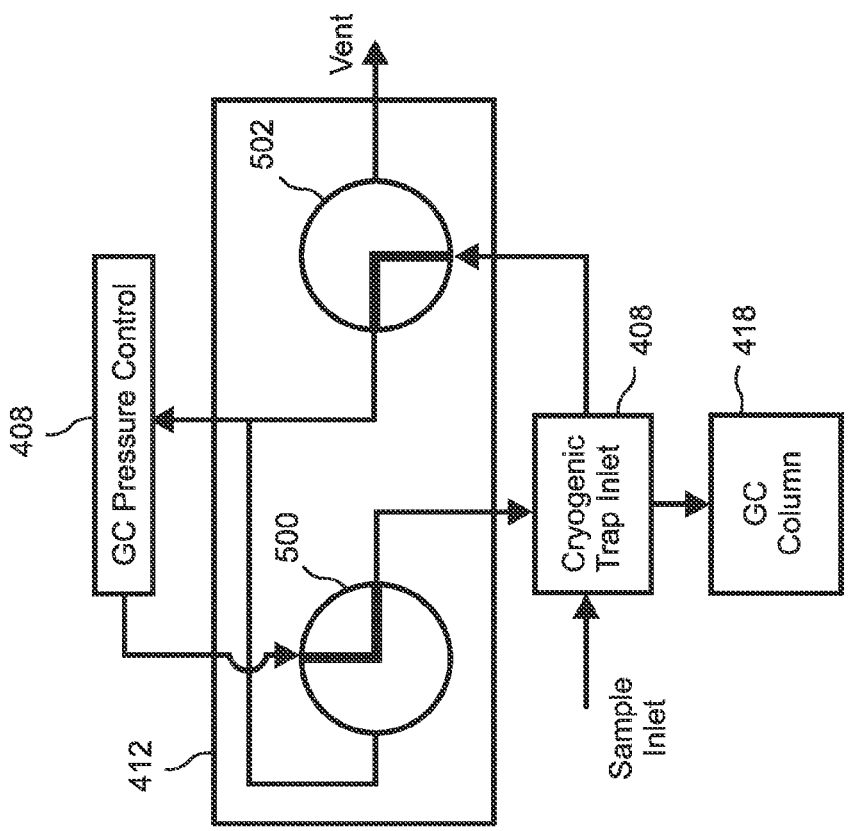
FIG. 5A is a block diagram of a carrier gas flow adaptor shown in the normal configuration.

FIGS. 5A and 5B are functional block diagrams that illustrate how two three-way valves 500, 502 are used in an embodiment of the carrier gas flow adaptor 412 to by-pass and short-circuit the cryogenic trap chamber 404 pressure control circulation system while carrier gas is delivered at a high flow rate from the desorption chamber 104 or 204 of the present invention to the cryogenic trap chamber 404. FIG. 5A shows the two valves 500, 502 in their "normal" positions, whereby the GC pressure controller 408 is connected to the cryogenic trap chamber 404. During delivery of the analytes from the desorption chamber 414 to the cryogenic trap chamber 404, the two valves 500, 502 are automatically switched to by-pass settings, as shown in FIG. 5B, and the carrier gas is released through the vent 416 either to atmosphere or to a partial vacuum, thus ameliorating system pressure buildup from the increased flow at the cryogenic trap 404 during the desorption process. After delivery of the analytes is completed, the flow of carrier gas is stopped, and the valves 500, 502 are automatically returned to their "normal" positions.

The foregoing description of the embodiments of the invention has been presented for the purposes of illustration and description. It is not intended to be exhaustive or to limit the invention to the precise form disclosed. Many modifications and variations are possible in light of this disclosure. It is intended that the scope of the invention be limited not by this detailed description, but rather by the claims appended hereto.

What is claimed is:

1. A system for rapidly desorbing analytes from a carbonaceous sorbent powder for introduction into a gas chromatograph, the system comprising:
   a sealed desorption chamber;
   a desorption surface within the desorption chamber onto which the sorbent powder can be deposited, the sorbent powder having analytes adsorbed thereupon;
   a transport gas system configured to transport the sorbent powder with a transport gas into the desorption chamber and to deposit the sorbent powder onto the desorption surface as a substantially uniform layer of sorbent powder granules, the transport gas system being further configured to remove the sorbent powder from the desorption chamber after desorption of the analytes therefrom;
   a heating light source located outside of the desorption chamber;
   a window included in a wall of the deposition chamber and positioned so as to allow light from the heating light source to uniformly illuminate all of the uniform monolayer of sorbent powder, absorption of the heating light by the sorbent powder causing desorption of the analytes therefrom; and
   an analyte removal system configured to transport desorbed analytes away from the sorbent powder out of the desorption chamber, and into the gas chromatograph, said analyte removal system being distinct from said transport gas system.

2. The system of claim 1, wherein the analyte removal system is a vacuum removal system configured to impose a partial vacuum in the desorption chamber and to allow the desorbed analytes to diffuse away from the sorbent and into the gas chromatograph.

3. The system of claim 1, wherein the analyte removal system is a carrier gas system configured to cause a carrier gas to flow into proximity with the sorbent powder and to carry the desorbed analytes away from the sorbent powder.

4. The system of claim 3, wherein the carrier gas is one of helium, argon, or carbon dioxide.

5. The system of claim 3, wherein the carrier gas system provides a carrier gas flow rate of 300 cc per minute with helium as the carrier gas.

6. The system of claim 3, further comprising a carrier gas flow adaptor configured to deliver the carrier gas and analytes to a cryogenic trap of the gas chromatograph and to vent the carrier gas after delivery of the analytes to the cryogenic trap, the adaptor being further configured to short-circuit a cryogenic trap pressure regulation system back onto itself and to isolate the pressure regulation system from the cryogenic trap while the analytes are being carried by the carrier gas into the cryogenic trap.

7. The system of claim 1, wherein the transport system is configured to deposit the sorbent powder onto the desorption surface as a substantially uniform monolayer of sorbent powder granules.

8. The system of claim 1 wherein the desorption surface is an inner surface of the window.

9. The system of claim 1, wherein the desorption chamber includes a porous frit that divides the desorption chamber into a lower section and an upper section.

10. The system of claim 9, wherein the porous frit is made of either glass or steel.

11. The system of claim 9, wherein a surface of the porous frit is the desorption surface.

12. The system of claim 1, wherein the desorption system includes a central pipe through which the transport gas carries the sorbent into the desorption chamber.

13. The system of claim 12, wherein the analyte removal system is a carrier gas system configured to cause a carrier gas to flow into proximity with the monolayer of sorbent powder and to carry the desorbed analytes away from the sorbent powder, and the carrier gas system introduces the carrier gas into the desorption chamber through the central pipe.

14. The system of claim 12, wherein the transport gas removes the sorbent powder from the desorption chamber through the central pipe.

15. The system of claim 1, wherein the transport gas is one of helium, argon, carbon dioxide, and nitrogen.

16. The system of claim 1, wherein the heating light source is a tungsten halogen lamp.

17. The system of claim 1, further comprising a heating system configured to heat the desorption chamber to a temperature above ambient.

18. The system of claim 17, wherein the heating system is configured to control a temperature of the desorption chamber according to a heating profile.

19. The system of claim 1, wherein the transport gas system is configured to divide the sorbent powder into a plurality of samples, and to deliver one of the samples to the desorption surface while withholding at least one of the samples from the desorption chamber.

20. A method for desorbing analytes from a carbonaceous sorbent powder and introducing the analytes into a gas chromatograph, the method comprising:
   causing a transport gas to deliver the carbonaceous sorbent powder with analytes adsorbed thereon onto a desorption surface within a desorption chamber, the sorbent powder being distributed onto the desorption surface as a substantially uniform layer of powder granules;
   uniformly illuminating substantially all of the sorbent granules simultaneously with a heating light delivered through a window in a wall of the desorption chamber from a light source located outside of the desorption chamber, absorption of the heating light by the powder granules causing desorption of the analytes therefrom;
   during the illumination of the sorbent powder, transporting the analytes away from the sorbent powder, out of the desorption chamber and into a gas chromatograph; and
   after desorption of the analytes and transporting of the analytes, causing the transport gas to remove the sorbent powder from the desorption chamber.

21. The method of claim 20, wherein transporting the analytes away from the sorbent powder, out of the desorption chamber and into a gas chromatograph includes creating a partial vacuum within the desorption chamber and allowing the desorbed analytes to diffuse away from the sorbent and into the gas chromatograph.

22. The method of claim 20, wherein transporting the analytes away from the sorbent powder, out of the desorption chamber and into a gas chromatograph includes causing a carrier gas to flow in proximity to the sorbent powder and thereby causing the carrier gas to carry the desorbed analytes away from the sorbent powder and into the gas chromatograph.

23. The method of claim 22, further comprising:
   isolating a GC pressure controller from a cryogenic trap while the carrier gas delivers the analytes to the cryogenic trap; and
   directly venting the carrier gas after it has delivered the analytes to the cryogenic trap.

24. The method of claim 20, wherein the sorbent powder is distributed onto the desorption surface as a substantially uniform monolayer of powder granules.

25. The method of claim 20, wherein the desorption surface is an inner surface of the window.

26. The method of claim 20, wherein the desorption chamber includes a porous frit that divides the desorption chamber into upper and lower sections and prevents sorbent powder from traveling together with the analytes through the frit and into the gas chromatograph.

27. The method of claim 26, wherein the desorption surface is a surface of the porous frit.

* * * * *